United States Patent [19]
Hadcock et al.

[11] Patent Number: 6,077,666
[45] Date of Patent: Jun. 20, 2000

[54] RECEPTOR IDENTIFICATION METHOD

[75] Inventors: John Richard Hadcock, Mt. Holly, N.J.; Bradley Alton Ozenberger, Yardley, Pa.; Mark Henry Pausch, Plainsboro, N.J.

[73] Assignee: American Cyanamid Company, Madison, N.J.

[21] Appl. No.: 08/853,194

[22] Filed: May 8, 1997

Related U.S. Application Data

[62] Division of application No. 07/915,966, Jul. 17, 1992, Pat. No. 5,668,006.

[51] Int. Cl.[7] .............................. C12Q 1/68; C12P 19/34
[52] U.S. Cl. ............................................... 435/6; 435/91.2
[58] Field of Search ....................... 435/6, 91.2; 536/23.1

[56] References Cited

PUBLICATIONS

Yamada et al. "Cloning and functional characterization of a family of human and mouse somatostatin receptors expressed in brain, gastrointestinal tract, and kidney" PNAS, vol. 89, pp. 251–255 Jan. 1992.

Lewis, et al. "A guanine nucleotide–binding protein mediates the inhibition of voltage–dependent calcium current by somatostatin in a pituitary cell line" PNAS, vol. 83, pp. 9035–9039 Dec. 1986.

Averyanov A., et. al. "Screening of fungicide activity" Abstract, WPI, Derwent Publications Ltd. Mar. 15, 1991.

Tsuboi Shinichi, et al. "Insecticidal and Fungicidal Composition for Agricultural use" Abstract, Derwent Publications Ltd. Apr. 2, 1988.

Maki Hirohisa, "Antibacterial Molding" Abstract, Derwent Publications Ltd. Feb. 28, 1992.

Tyuterev S. et al., Verticillium–Dahliae–Phytopathogen Synthesis Fungicide Agriculturej Phytoalexins, Abstract, Database Biosis, pp. 405–416, vol. 25, No. 5, 1989.

*Primary Examiner*—Eggerton A. Campbell
*Attorney, Agent, or Firm*—Gale Matthews; Milagros A. Cepeda

[57] ABSTRACT

The present invention relates to a method for isolating and cloning receptor DNA sequences. The invention also provides novel DNA sequences encoding a novel somatostatin receptor subtype.

7 Claims, 11 Drawing Sheets

Stage 1. PCR & preliminary characterization of DNA fragments.

-PCR-  Template = tissue-specific cDNA
6 different primer sets

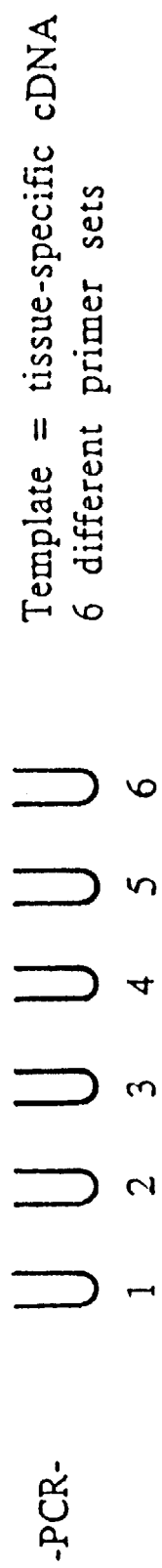

-DNA analysis-  Clone PCR products
Determine nucleotide sequence
Compare to GenBank - identify G protein-linked receptor sequences
- eliminate previously cloned genes

Result: Pool of unidentified G protein-linked receptor gene fragments
derived from a known tissue (*e.g.*, pituitary or adipose)

*FIG. 1*

Stage 2. Antisense oligonucleotide synthesis and effector assays.
-synthesize oligos- Synthesize sense and antisense oligos derived from each orphan PCR fragment
-effector assays-
| | | | | | | | | | Responsive cells Hormone |
|---|---|---|---|---|---|---|---|---|---|
| TUBE | 1 | 2 | 3 | 4 | 5 | 6 | 7 | 8 | |
| ORPHAN | #1 | #1 | #2 | #2 | #3 | #3 | #4 | #4 | |
| OLIGO SENSE | + | − | + | − | + | − | + | − | |
| cAMP | ↑ | ↑ | ↑ | ↑ | ↑ | 0 | ↑ | ↑ | |
FIG. 1cont.

| Designation | Location | Length | Degeneracy | Nucleotide Sequence |
|---|---|---|---|---|
| #8 | tm2 | 26 | 16X; 23% I | TWCTTSTMACCTGGYCTTGCTGA |
| #9 | tm3 | 25 | 4X; 12% I | TGTTYTCCAGCATCTACTTMTGAC |
| #10 | tm6 | 26 | 64X; 19% I | ATGRTGATSITKGTNGTGTKKRTTT |
| #11 | tm6 | 20 | 4X; 5% I | TTYGYCATCTGCTGGTTGCC |
| #12 | tm7 | 17 | 8X; 6% I | AAYAGCTGYGCCAASCC |

| Designation | Location | Length | Degeneracy | Nucleotide Sequence |
|---|---|---|---|---|
| #13 | 5' | 21 | 8X; 24% I | TGGGARICATKIIITGYTGG |
| #14 | tm3 | 19 | 4X; 16% I | GAIGGISTCTAICTTCAYA |
| #15 | tm6 | 19 | 16X; 21% I | ASTGIAYICCIARIAGSGG |
| #16 | tm7 | 22 | 2X; 23% I | CYTCICIITGIIGAAICAGTA |

PCR9

TTCGTGGTGA ACCTGGTCGG GGCTGACTTT CTCCTGATCA TTTGCTTGCC GTTCTTGACG
GACAACTATG TCCAGAACTG GGACTGGAGG TTCGGGAGCA TCCCCTGCCG CGTGATGCTC
TTCATGTTGG CCATGAACCG ACAGGGCAGC ATCATCTTCC TCACGGTGGT GGCTGTGGAC
AGGTACTTCA GGGTGGTCCA CCCGCACCAC AGATCTCCAA CCGGACGGCG
GCCATCATCT CTTGCTTCCT GTGGGGCATC ACCATCCGCC CCTCCTCTAC
ACGGACATGA TGACCCGAAA CGGCGATGCA AACCTGTGCA GCAGTTTTAG CATCTGCTAC
ACTTTCAGGT GGCACGGATG AATGTTCCTC TTGGAATTCT TCCTGCCCCT GGGCATCATC
CTGTTCTGCT CTGGCAGGAT CATTTGGAGC CTAAGGCAGA GACAGATGGA CAGGCACGTC
AAGATCAAGA GGGCCATCAA CTTCATCATG GTGGTTGCCA TTGTGTTTGC CATCTGCTGG
CTGCC

FIG. 3

PCR11

TTCGTGCTGC ACCTGGTCGG GGCTGACGTA TTATTTATGT TGGGACTTCC TTTCCTGGCC
ACGCAGAACG CCGTCTCCTA CTGGCCCTTC GGCTCCTTCT TGTGCCGCCT GGTCATGACA
CTGGATGGCA TCAACCAGTT CACCAGTATC TTCTGCCTGA TGGTCATGAG TGTTGACCGC
TACCTGGCCG TGGTCCACCC TCTCCGCTCA GCCCGGTGGC GTCGCCCACG GGTAGCCAAG
ATGGCCAGCG CGGCCGTCTG GGTCTTTTCG CTGCTCATGT CTCTGCCGCT CTTGGTCTTC
GCGGATGTCC AGGAGGGCTG GGGCACCTGC AACCTGAGCT GGCCAGAGCC TGTGGGGCTG
TGGGGTGCAG CCTTCATCAC CTACACGTCT GTGTTGGGCT TCTTTGGGCC CCTGCTGGTC
ATCTGCTTGT GCTACCTGCT CATTGTGGTC CTGCAGGCAT GCGCGTAGGC
TCCTCAAGGC GGAGACGCTC GGAGCGCAAG AAGGTGAAGG GTGACTCGCA TGGTGGTGGT CGTGGTGCTG
GTGTTCGCCA TCTGCTCTGGCT GCC

FIG. 3 cont.

PCR9

PCR11

```
TTCGTGCTGA ACCTGGCCGG GGCTGACGTG TTGTTTATGT TGGGGCTTCC TTTCCTGGCA   60
ACGCAGAATG CTGTCTCCTA CTGGCCCTTT GGCTCCTTCT TGTGCCGCCT GGTCATGACG  120
CTGGACGGCA TCAACCAGTT CACCAGTATC TTCTGCCTGA TGGTCGACCG TGTCGACCGC  180
TACCTGGCCG TGGTCCACCC TCTCCGCTCA GCCCGGTGGC GTCGCCCACG GGTAGCCAAG  240
CTGGCTAGTG CTGCCGTCTG GGTCTTCTCG CTGCTCATGT CTCTGCCGCT CTTGGTCTTT  300
GCGGATGTCC AGGAGGGCTG GGGCAACTGC AACCTGAGCT GGCCAGAGCC TGTGGGAATG  360
TGGGGTGCAG CCTTCATCAC TTACACGTCT GTGCTGGGCT TCTTTGGGCC CCTGCTGGTC  420
ATCTGCATGT GCTATTTGCT CATCGTAGTG AAGGTGAAGG CTGCAGGTAT GCCGTGTGGC  480
TCCTCACGGC GCAGGCGCTC AGAACCCAAG GTGACTCGCA TGGTGGTGGT AGTGGTGCCG  540
CTGTTCGTGG GCTGCTGGCT GCCTTTCTTC ATCGTCAACA TCGTCAACCT GGCCTTCACG  600
CTACCCGAGG AGCCCACCTC TGCCGGCCTC TACTTCTTTG TGGTGGTCCT GTCTTATGCC  660
AATAGCCGCG CCAAGCCC
```

FIG. 7

```
                    2                              3
SSTR3   VLFMLGLPFLATQNAVSYWPFGSFLCRLVMTLDGINQFTS
    2   E----------M-V-lVH----KAi--v---v--------
    1   E-l--Sv---V-STLlRH----Al-----lSv-Av-M---

SSTR3   IFCLMVMSVDRYLAVVHPLRSARWRRPRVAKLASAAVWVF
    2   ----T---i----------ik--k-----T--mINV---CV
    1   -y--T-l-----v-----ikA--Y---T---vVNLG---l

4
SSTR3   SLLMSLPLLVFADVQEGWGNCNLSWPEPVGMWGAAFITYT
    2   ---vI--imiy-GlRNQ--S-TiN--GES-A-YTG---I-A
    1   ---vI--iv---ANSd-TVA--mLM---AQR-LVG-vL--

5
SSTR3   SVLGFFGPLLVICMCYLLIVVKVKAAGMRVGSSRRRRSEP
    2   Fi---lV--Ti--l---f-ii---SS-i-----k-kk--K
    1   Flm--lL-vGA--l--v--iA-mrMVAlkA-WQQ-k---R

6
SSTR3   KVTRMVVVVVRLFVGCWLPFFIVNIVNLAFTLPEEPTSAG
    2   ------Si--Av-iF-----y-F-vSSvSVAiSPT-ALK-
    1   -i-L--mm--Mv--I--m--yv-Ql--v -AEQddA-VSQ

7
SSTR3   LYFFVVVLSYA
    2   mfD---i-T--
    1   -   S-i-G--
```

FIG. 8

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 545 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Rat (x) PUBLICATION INFORMATION:
       (A) AUTHORS: Hadcock Dr., John R.
           Dr. Ozenberger, Bradley A.
           Dr. Pausch, Mark
       (B) TITLE: Receptor Identification Method
       (G) DATE: 17-JUL-1992

(xi) SEQUENCE DESCRIPTION: SEQ ID NO:1:

| | | | | | |
|---|---|---|---|---|---|
| TTCGTGGTGA | ACCTGGTCGG | GGCTGACTTT | CTCCTGATCA | TTTGCTTGCC | GTTCTTGACG | 60 |
| GACAACTATG | TCCAGAACTG | GGACTGGAGG | TTCGGGAGCA | TCCCCTGCCG | CGTGATGCTC | 120 |
| TTCATGTTGG | CCATGAACCG | ACAGGGCAGC | ATCATCTTCC | TCACGGTGGT | GGCTGTGGAC | 180 |
| AGGTACTTCA | GGGTGGTCCA | CCCGCACCAC | TTCCTGAACA | AGATCTCCAA | CCGGACGGCG | 240 |
| GCCATCATCT | CTTGCTTCCT | GTGGGGCATC | ACCATCGGCC | TGACAGTCCA | CCTCCTCTAC | 300 |
| ACGGACATGA | TGACCCGAAA | CGGCGATGCA | AACCTGTGCA | GCAGTTTTAG | CATCTGCTAC | 360 |
| ACTTTCAGGT | GGCACGATGC | AATGTTCCTC | TTGGAATTCT | TCCTGCCCCT | GGGCATCATC | 420 |
| CTGTTCTGCT | CTGGCAGGAT | CATTTGGAGC | CTAAGGCAGA | GACAGATGGA | CAGGCACGTC | 480 |
| AAGATCAAGA | GGGCCATCAA | CTTCATCATG | GTGGTTGCCA | TTGTGTTTGC | CATCTGCTGG | 540 |
| CTGCC | | | | | | 545 |

(2) INFORMATION FOR SEQ ID NO:2:

(i) SEQUENCE CHARACTERISTICS:
       (A) LENGTH: 563 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Rat (xi) SEQUENCE DESCRIPTION: SEQ ID NO:2:

| | | | | | |
|---|---|---|---|---|---|
| TTCGTGCTGC | ACCTGGTCGG | GGCTGACGTA | TTATTTATGT | TGGGACTTCC | TTTCCTGGCC | 60 |
| ACGCAGAACG | CCGTCTCCTA | CTGGCCCTTC | GGCTCCTTCT | TGTGCCGCCT | GGTCATGACA | 120 |
| CTGGATGGCA | TCAACCAGTT | CACCAGTATC | TTCTGCCTGA | TGGTCATGAG | TGTTGACCGC | 180 |

-continued

```
TACCTGGCCG TGGTCCACCC TCTCCGCTCA GCCCGGTGGC GTCGCCCACG GGTAGCCAAG      240

ATGGCCAGCG CGGCCGTCTG GGTCTTTTCG CTGCTCATGT CTCTGCCGCT CTTGGTCTTC      300

GCGGATGTCC AGGAGGGCTG GGGCACCTGC AACCTGAGCT GGCCAGAGCC TGTGGGGCTG      360

TGGGGTGCAG CCTTCATCAC CTACACGTCT GTGTTGGGCT TCTTTGGGCC CCTGCTGGTC      420

ATCTGCTTGT GCTACCTGCT CATTGTGGTC AAGGTGAAGG CTGCAGGCAT GCGCGTAGGC      480

TCCTCAAGGC GGAGACGCTC GGAGCGCAAG GTGACTCGCA TGGTGGTGGT CGTGGTGCTG      540

GTGTTCGCCA TCTGCTGGCT GCC                                              563
```

(2) INFORMATION FOR SEQ ID NO:3:

(i) SEQUENCE CHARACTERISTICS:
        (A) LENGTH: 678 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Mouse (xi) SEQUENCE DESCRIPTION: SEQ ID NO:3:

```
TTCGTGCTGA ACCTGGCCGG GGCTGACGTG TTGTTTATGT TGGGGCTTCC TTTCCTGGCA       60

ACGCAGAATG CTGTCTCCTA CTGGCCCTTT GGCTCCTTCT TGTGCCGCCT GGTCATGACG      120

CTGGACGGCA TCAACCAGTT CACCAGTATC TTCTGCCTGA TGGTCATGAG TGTCGACCGC      180

TACCTGGCCG TGGTCCACCC TCTCCGCTCA GCCCGGTGGC GTCGCCCACG GGTAGCCAAG      240

CTGGCTAGTG CTGCCGTCTG GGTCTTCTCG CTGCTCATGT CTCTGCCGCT CTTGGTCTTT      300

GCGGATGTCC AGGAGGGCTG GGCAACTGC AACCTGAGCT GGCCAGAGCC TGTGGGAATG       360

TGGGGTGCAG CCTTCATCAC TTACACGTCT GTGCTGGGCT TCTTTGGGCC CCTGCTGGTC      420

ATCTGCATGT GCTATTTGCT CATCGTAGTG AAGGTGAAGG CTGCAGGTAT GCGTGTGGGC      480

TCCTCACGGC GGAGGCGCTC AGAACCCAAG GTGACTCGCA TGGTGGTGGT AGTGGTGCGG      540

CTGTTCGTGG GCTGCTGGCT GCCTTTCTTC ATCGTCAACA TCGTCAACCT GGCCTTCACG      600

CTACCCGAGG AGCCCACCTC TGCCGGCCTC TACTTCTTTG TGGTGGTCCT GTCTTATGCC      660

AATAGCCGCG CCAAGCCC                                                   678
```

(2) INFORMATION FOR SEQ ID NO:4:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Rat -continued (xi) SEQUENCE DESCRIPTION: SEQ ID NO:4:

```
Val Leu Phe Met Leu Gly Leu Pro Phe Leu Ala Thr Gln Asn Ala Val
1               5                   10                  15

Ser Tyr Trp Pro Phe Gly Ser Phe Leu Cys Arg Leu Val Met Thr Leu
            20                  25                  30

Asp Gly Ile Asn Gln Phe Thr Ser Ile Phe Cys Leu Met Val Met Ser
            35                  40                  45

Val Asp Arg Tyr Leu Ala Val Val His Pro Leu Arg Ser Ala Arg Trp
50                  55                  60

Arg Arg Pro Arg Val Ala Lys Leu Ala Ser Ala Ala Val Trp Val Phe
65                  70                  75                  80

Ser Leu Leu Met Ser Leu Pro Leu Leu Val Phe Ala Asp Val Gln Glu
                85                  90                  95

Gly Trp Gly Asn Cys Asn Leu Ser Trp Pro Glu Pro Val Gly Met Trp
                100                 105                 110

Gly Ala Ala Phe Ile Thr Tyr Thr Ser Val Leu Gly Phe Phe Gly Pro
            115                 120                 125

Leu Leu Val Ile Cys Met Cys Tyr Leu Leu Ile Val Val Lys Val Lys
            130                 135                 140

Ala Ala Gly Met Arg Val Gly Ser Ser Arg Arg Arg Arg Ser Glu Pro
145                 150                 155                 160

Lys Val Thr Arg Met Val Val Val Val Arg Leu Phe Val Gly Cys
                165                 170                 175

Trp Leu Pro Phe Phe Ile Val Asn Ile Val Asn Leu Ala Phe Thr Leu
                180                 185                 190

Pro Glu Glu Pro Thr Ser Ala Gly Leu Tyr Phe Phe Val Val Val Leu
                195                 200                 205

Ser Tyr Ala
    210
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Synthetic (x) PUBLICATION INFORMATION:
        (A) AUTHORS: Hadcock Dr., John R.
            Dr. Ozenberger, Bradley A.
            Dr. Pausch, Mark
        (B) TITLE: Receptor Identification Method
        (G) DATE: 17-JUL-1992

(xi) SEQUENCE DESCRIPTION: SEQ ID NO:5:

GGGTCGCCTC CATTTCGG                                            18

(2) INFORMATION FOR SEQ ID NO:6:

(i) SEQUENCE CHARACTERISTICS:
        (A) LENGTH: 18 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (x) PUBLICATION INFORMATION:
        (A) AUTHORS: Hadcock Dr., John R.
              Dr. Ozenberger, Bradley A.
              Dr. Pausch, Mark
        (B) TITLE: Receptor Identification Method
        (G) DATE: 17-JUL-1992

(xi) SEQUENCE DESCRIPTION: SEQ ID NO:6:

GCCAAATGGA GGCGACCC                                                    18

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Synthetic (x) PUBLICATION INFORMATION:
        (A) AUTHORS: Hadcock Dr., John R.
              Dr. Ozenberger, Bradley A.
              Dr. Pausch, Mark
        (B) TITLE: Receptor Identification Method
        (G) DATE: 17-JUL-1992

(xi) SEQUENCE DESCRIPTION: SEQ ID NO:7:

CGAGCGCCTC CGCCTTGAGG                                                  20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic (x) PUBLICATION INFORMATION:
        (A) AUTHORS: Hadcock Dr., John R.
              Dr. Ozenberger, Bradley A.
              Dr. Pausch, Mark
        (B) TITLE: Receptor Identification Method
        (G) DATE: 17-JUL-1992

(xi) SEQUENCE DESCRIPTION: SEQ ID NO:8:
```

```
ACGCAGAACG CCGTCTCCTA                                                        20

(2) INFORMATION FOR SEQ ID NO:9:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Synthetic (ix) FEATURE:
         (A) NAME/KEY: modified_base
         (B) LOCATION: 4
         (D) OTHER INFORMATION: /mod_base= i (ix) FEATURE:
         (A) NAME/KEY: modified_base
         (B) LOCATION: 6
         (D) OTHER INFORMATION: /mod_base= i (ix) FEATURE:
         (A) NAME/KEY: modified_base
         (B) LOCATION: 9
         (D) OTHER INFORMATION: /mod_base= i (ix) FEATURE:
         (A) NAME/KEY: modified_base
         (B) LOCATION: 19..21
         (D) OTHER INFORMATION: /mod_base= i (x) PUBLICATION INFORMATION:
         (A) AUTHORS: Hadcock Dr., John R.
             Dr. Ozenberger, Bradley A.
             Dr. Pausch, Mark
         (B) TITLE: Receptor Identification Method
         (G) DATE: 17-JUL-1992

(xi) SEQUENCE DESCRIPTION: SEQ ID NO:9:

TWCNTNSTNM ACCTGGYCNN NGCTGA                                                 26

(2) INFORMATION FOR SEQ ID NO:10:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Synthetic (ix) FEATURE:
         (A) NAME/KEY: modified_base
         (B) LOCATION: 6
         (D) OTHER INFORMATION: /mod_base= i (ix) FEATURE:
         (A) NAME/KEY: modified_base
         (B) LOCATION: 19..20
         (D) OTHER INFORMATION: /mod_base= i
```

(x) PUBLICATION INFORMATION:
            (A) AUTHORS: Hadcock Dr., John R.
                Dr. Ozenberger, Bradley A.
                Dr. Pausch, Mark
            (B) TITLE: Receptor Identification Method
            (G) DATE: 17-JUL-1992

(xi) SEQUENCE DESCRIPTION: SEQ ID NO:10:

TGTTYNCCAG CATCTACTNN MTGAC                                                    25

(2) INFORMATION FOR SEQ ID NO:11:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Synthetic (ix) FEATURE:
            (A) NAME/KEY: modified_base
            (B) LOCATION: 10
            (D) OTHER INFORMATION: /mod_base= i (ix) FEATURE:
            (A) NAME/KEY: modified_base
            (B) LOCATION: 19
            (D) OTHER INFORMATION: /mod_base= i (ix) FEATURE:
            (A) NAME/KEY: modified_base
            (B) LOCATION: 23..24
            (D) OTHER INFORMATION: /mod_base= i (x) PUBLICATION INFORMATION:
            (A) AUTHORS: Hadcock Dr., John R.
                Dr. Ozenberger, Bradley A.
                Dr. Pausch, Mark
            (B) TITLE: Receptor Identification Method
            (G) DATE: 17-JUL-1992

(xi) SEQUENCE DESCRIPTION: SEQ ID NO:11:

ATGRTGATSN TKGTNGTGNK KRNNTT                                                   26

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Synthetic (ix) FEATURE:
            (A) NAME/KEY: modified_base
            (B) LOCATION: 16
            (D) OTHER INFORMATION: /mod_base= i (x) PUBLICATION INFORMATION:

(A) AUTHORS: Hadcock Dr., John R.
                Dr. Ozenberger, Bradley A.
                Dr. Pausch, Mark
            (B) TITLE: Receptor Identification Method
            (G) DATE: 17-JUL-1992

(xi) SEQUENCE DESCRIPTION: SEQ ID NO:12:

TTYGYCATCT GCTGGNTGCC                                                   20

(2) INFORMATION FOR SEQ ID NO:13:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Synthetic (ix) FEATURE:
         (A) NAME/KEY: modified_base
         (B) LOCATION: 7
         (D) OTHER INFORMATION: /mod_base= i (x) PUBLICATION INFORMATION:
         (A) AUTHORS: Hadcock Dr., John R.
             Dr. Ozenberger, Bradley A.
             Dr. Pausch, Mark
         (B) TITLE: Receptor Identification Method
         (G) DATE: 17-JUL-1992

(xi) SEQUENCE DESCRIPTION: SEQ ID NO:13:

AAYAGCNGYG CCAASCC                                                      17

(2) INFORMATION FOR SEQ ID NO:14:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Synthetic (ix) FEATURE:
         (A) NAME/KEY: modified_base
         (B) LOCATION: 6
         (D) OTHER INFORMATION: /mod_base= i (ix) FEATURE:
         (A) NAME/KEY: modified_base
         (B) LOCATION: 8
         (D) OTHER INFORMATION: /mod_base= i (ix) FEATURE:
         (A) NAME/KEY: modified_base
         (B) LOCATION: 13..15
         (D) OTHER INFORMATION: /mod_base= i (x) PUBLICATION INFORMATION:
         (A) AUTHORS: Hadcock Dr., John R.

```
            Dr. Ozenberger, Bradley A.
            Dr. Pausch, Mark
     (B) TITLE: Receptor Identification Method
     (G) DATE: 17-JUL-1992

(xi) SEQUENCE DESCRIPTION: SEQ ID NO:14:

TGGGANRNCA TKNNNTGYTG G                                        21

(2) INFORMATION FOR SEQ ID NO:15:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (ix) FEATURE:
       (A) NAME/KEY: modified_base
       (B) LOCATION: 3
       (D) OTHER INFORMATION: /mod_base= i (ix) FEATURE:
       (A) NAME/KEY: modified_base
       (B) LOCATION: 6
       (D) OTHER INFORMATION: /mod_base= i (ix) FEATURE:
       (A) NAME/KEY: modified_base
       (B) LOCATION: 12
       (D) OTHER INFORMATION: /mod_base= i (x) PUBLICATION INFORMATION:
       (A) AUTHORS: Hadcock Dr., John R.
            Dr. Ozenberger, Bradley A.
            Dr. Pausch, Mark
       (B) TITLE: Receptor Identification Method
       (G) DATE: 17-JUL-1992

(xi) SEQUENCE DESCRIPTION: SEQ ID NO:15:

GANGGNSTCT ANCTTCAYA                                           19

(2) INFORMATION FOR SEQ ID NO:16:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Synthetic (ix) FEATURE:
       (A) NAME/KEY: modified_base
       (B) LOCATION: 5
       (D) OTHER INFORMATION: /mod_base= i (ix) FEATURE:
       (A) NAME/KEY: modified_base
       (B) LOCATION: 8
```

(D) OTHER INFORMATION: /mod_base= i (ix) FEATURE:
          (A) NAME/KEY: modified_base
          (B) LOCATION: 11
          (D) OTHER INFORMATION: /mod_base= i (ix) FEATURE:
          (A) NAME/KEY: modified_base
          (B) LOCATION: 14
          (D) OTHER INFORMATION: /mod_base= i (x) PUBLICATION INFORMATION:
          (A) AUTHORS: Hadcock Dr., John R.
               Dr. Ozenberger, Bradley A.
               Dr. Pausch, Mark
          (B) TITLE: Receptor Identification Method
          (G) DATE: 17-JUL-1992

(xi) SEQUENCE DESCRIPTION: SEQ ID NO:16:

ASTGNAYNCC NARNAGSGG                                                      19

(2) INFORMATION FOR SEQ ID NO:17:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Synthetic (ix) FEATURE:
          (A) NAME/KEY: modified_base
          (B) LOCATION: 5
          (D) OTHER INFORMATION: /mod_base= i (ix) FEATURE:
          (A) NAME/KEY: modified_base
          (B) LOCATION: 8
          (D) OTHER INFORMATION: /mod_base= i (ix) FEATURE:
          (A) NAME/KEY: modified_base
          (B) LOCATION: 12..13
          (D) OTHER INFORMATION: /mod_base= i (ix) FEATURE:
          (A) NAME/KEY: modified_base
          (B) LOCATION: 17
          (D) OTHER INFORMATION: /mod_base= i (x) PUBLICATION INFORMATION:
          (A) AUTHORS: Hadcock Dr., John R.
               Dr. Ozenberger, Bradley A.
               Dr. Pausch, Mark
          (B) TITLE: Receptor Identification Method
          (G) DATE: 17-JUL-1992

(xi) SEQUENCE DESCRIPTION: SEQ ID NO:17:

CYTCNCCNTT GNNGAANCAG TA                                                  22

(2) INFORMATION FOR SEQ ID NO:18:

(i) SEQUENCE CHARACTERISTICS:
          (A) LENGTH: 211 amino acids
          (B) TYPE: amino acid
          (C) STRANDEDNESS: single

```
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: Mouse (xi) SEQUENCE DESCRIPTION: SEQ ID NO:18:

Glu Leu Phe Met Leu Gly Leu Pro Phe Leu Ala Met Gln Val Ala Leu
1               5                  10                  15

Val His Trp Pro Phe Gly Lys Ala Ile Cys Arg Val Val Met Thr Val
                20                  25                  30

Asp Gly Ile Asn Gln Phe Thr Ser Ile Phe Cys Leu Thr Val Met Ser
            35                  40                  45

Ile Asp Arg Tyr Leu Ala Val Val His Pro Ile Lys Ser Ala Lys Trp
    50                  55                  60

Arg Arg Pro Arg Thr Ala Lys Met Ile Asn Val Ala Val Trp Cys Val
65                  70                  75                  80

Ser Leu Leu Val Ile Leu Pro Ile Met Ile Tyr Ala Gly Leu Arg Asn
                85                  90                  95

Gln Trp Gly Ser Cys Thr Ile Asn Trp Pro Gly Glu Ser Gly Ala Trp
               100                 105                 110

Tyr Thr Gly Phe Ile Ile Tyr Ala Phe Ile Leu Gly Phe Leu Val Pro
           115                 120                 125

Leu Thr Ile Ile Cys Leu Cys Tyr Leu Phe Ile Ile Ile Lys Val Lys
   130                 135                 140

Ser Ser Gly Ile Arg Val Gly Ser Ser Lys Arg Lys Lys Ser Glu Lys
145                 150                 155                 160

Lys Val Thr Arg Met Val Ser Ile Val Val Ala Val Phe Ile Phe Cys
                165                 170                 175

Trp Leu Pro Phe Tyr Ile Phe Asn Val Ser Ser Val Ser Val Ala Ile
               180                 185                 190

Ser Pro Thr Pro Ala Leu Lys Gly Met Phe Asp Phe Val Val Ile Leu
           195                 200                 205

Thr Tyr Ala
   210

(2) INFORMATION FOR SEQ ID NO:19:

(i) SEQUENCE CHARACTERISTICS:
         (A) LENGTH: 211 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: Human (xi) SEQUENCE DESCRIPTION: SEQ ID NO:19:
```

-continued

```
Glu Leu Leu Met Leu Ser Val Pro Phe Leu Val Thr Ser Thr Leu Leu
1               5                   10                  15

Arg His Trp Pro Phe Gly Ala Leu Leu Cys Arg Leu Val Leu Ser Val
            20                  25              30

Asp Ala Val Asn Met Phe Thr Ser Ile Tyr Cys Leu Thr Val Leu Ser
        35                  40                  45

Val Asp Arg Tyr Val Ala Val Val His Pro Ile Lys Ala Ala Arg Tyr
    50                  55                  60

Arg Arg Pro Thr Val Ala Lys Val Val Asn Leu Gly Val Trp Val Leu
65              70                  75                      80

Ser Leu Leu Val Ile Leu Pro Ile Val Val Phe Ala Ala Asn Ser Asp
                85                  90                  95

Gly Thr Val Ala Cys Asn Met Leu Met Pro Glu Pro Ala Gln Arg Trp
            100                 105                 110

Leu Val Gly Phe Val Leu Tyr Thr Phe Leu Met Gly Phe Ile Leu Pro
            115                 120                 125

Val Gly Ala Ile Cys Leu Cys Tyr Val Leu Ile Ile Ala Lys Met Arg
    130                 135                 140

Met Val Ala Leu Lys Ala Gly Trp Gln Gln Arg Lys Arg Ser Glu Arg
145                 150                 155                 160

Lys Ile Thr Leu Met Val Met Met Val Val Met Val Phe Val Ile Cys
            165                 170                 175

Trp Met Pro Phe Tyr Val Val Gln Leu Val Asn Val Ala Phe Ala Glu
            180                 185                 190

Gln Asp Asp Ala Thr Val Ser Gln Leu Tyr Phe Phe Ser Val Ile Leu
        195                 200                 205

Gly Tyr Ala
        210
```

RECEPTOR IDENTIFICATION METHOD

This is a division of application(s) Ser. No. 07/915,966 filed on Jul. 17, 1992 now U.S. Pat. No. 5,668,066.

The superfamily of G protein-linked receptors controls many physiological functions. These receptors mediate transmembrane signaling from external stimuli (vision, taste and smell), endocrine function (pituitary and adrenal), exocrine function (pancreas), heart rate, lipolysis, and carbohydrate metabolism. The molecular cloning of only a fraction of the genes for this family has revealed many structural and genetic similarities including seven membrane spanning domains, conserved amino acids critical for function, and sites for glycosylation and phosphorylation. In many cases, the genes for these receptors lack introns, a rarity among eukaryotic genes. The G protein-linked receptor superfamily can be subclassified into five distinct groups: (i) amine receptors (serotonin, adrenergic, etc.); (ii) small peptide hormone (somatostatin, TRH, etc.); (iii) large peptide hormone (LH-CG, PSH, etc.); (iv) secretin family; and (v) odorant receptors (2). The isolation of as yet uncloned receptors that are associated with important physiological functions or disease states, or which are critical for enhancement of animal performance [e.g., receptors for growth hormone release factor, corticotropin release factor, cholecystokinin, vasoactive intestinal peptide (high affinity subtype)] would be highly beneficial.

Current strategies for cloning members of this receptor superfamily are diverse and fraught with difficulties. These techniques require the isolation of a full-length cDNA or gene to determine whether a particular protein is actually the receptor of interest. For example, expression cloning using a heterologous system (such as Xenopus oocytes) requires the isolation of the full-length cDNA (15). The use of PCR with degenerate oligonucleotides has also been used to clone G protein-linked receptors. However, this approach has been largely applied only to amine receptors, and not to peptide hormone receptors (9). A major drawback to that methodology is the generation of "orphan" receptors where the identification of the receptor, via identification of the hormone that activates it, may remain unknown for years. Finally, protein purification is difficult because these receptors are, in general, very low in abundance. Obtaining peptide sequence data is, therefore, an arduous and time-consuming task. In contrast, the present application describes a system that does not require isolation of a full-length cDNA until a PCR fragment has already been identified as originating from that gene. Additionally, utilization of the highly processive PCR technique, in combination with other steps, circumvents any difficulties due to low abundance.

SUMMARY OF THE INVENTION

The present invention relates to a method for isolation and identification of novel receptor DNA. The method comprises steps of (a) contacting a template nucleic acid, in a polymerase chain reaction, with at least one target receptor-specific oligonucleotide primer, and isolating a nucleic acid fragment resulting from the reaction; (b) providing an antisense oligonucleotide based on a nucleotide sequence from the isolated fragment to a cell capable of expressing a particular receptor, and (c) observing the presence or absence of the particular receptor's expression or function, in that cell. The absence of receptor expression indicates that the antisense oligo has blocked that receptor's expression, thereby confirming the identity of the isolated nucleic acid fragment upon which the antisense oligo was based as encoding all or a portion of the receptor whose expression has just been measured.

The present method is useful for identifying receptors from virtually any class, but is particularly useful in identification and isolation of G protein-linked receptor. For use in identification of this receptor type, the invention also provides a series of several novel oligonucleotides useful as primers in the first step polymerase chain reaction. The method has also resulted in the identification of a heretofore unknown somatostatin receptor subtype, herein designated as SSTR3; the invention therefore also provides a nucleic acid sequence encoding that receptor, as well as vectors and host cells capable of expressing the sequence.

The present invention provides significant advantages over known methods of receptor sequence isolation and cloning. It provides an alternative to the process of isolating receptor protein in order to obtain sequence information, a task which is necessarily arduous because of the frequently small amounts of expressed receptor in most cells; the use of PCR in the present method overcomes this problem. The ease of identification of the present method also avoids the classic problem of "orphan receptors", i.e., isolated nucleic acid fragments presumed to encode a receptor protein, but the identity of which remains unknown for lack of a reliable assay and/or a complete sequence. The claimed method provides a means for immediately identifying the ligand specificity of the isolated fragment by quick assay of its activity in wild-type cells and further avoids the necessity for having a full-length cDNA clone for heterologous expression in a host cell.

BRIEF DESCRIPTION OF THE FIGURES

FIG. 1. Procedure summary. In this example, four orphan G protein-linked receptor gene fragments are isolated. Vehicle, sense (+; as a negative control) and antisense oligos (−) derived from each clone are tested in a cAMP accumulation assay to determine if one attenuates the response to a ligand known to activate adenylyl cyclase. In this case, an antisense oligo to orphan #3 represses the response, thereby identifying that sequence as a portion of the gene encoding the assayed receptor.

FIG. 3. Nucleotide sequences of orphan receptor DNA fragments. Underlined sequences indicate PCR primers. Both fragments contain oligo #8 at the 5' terminus and oligo #10 at the 3' terminus.

Figure 6:
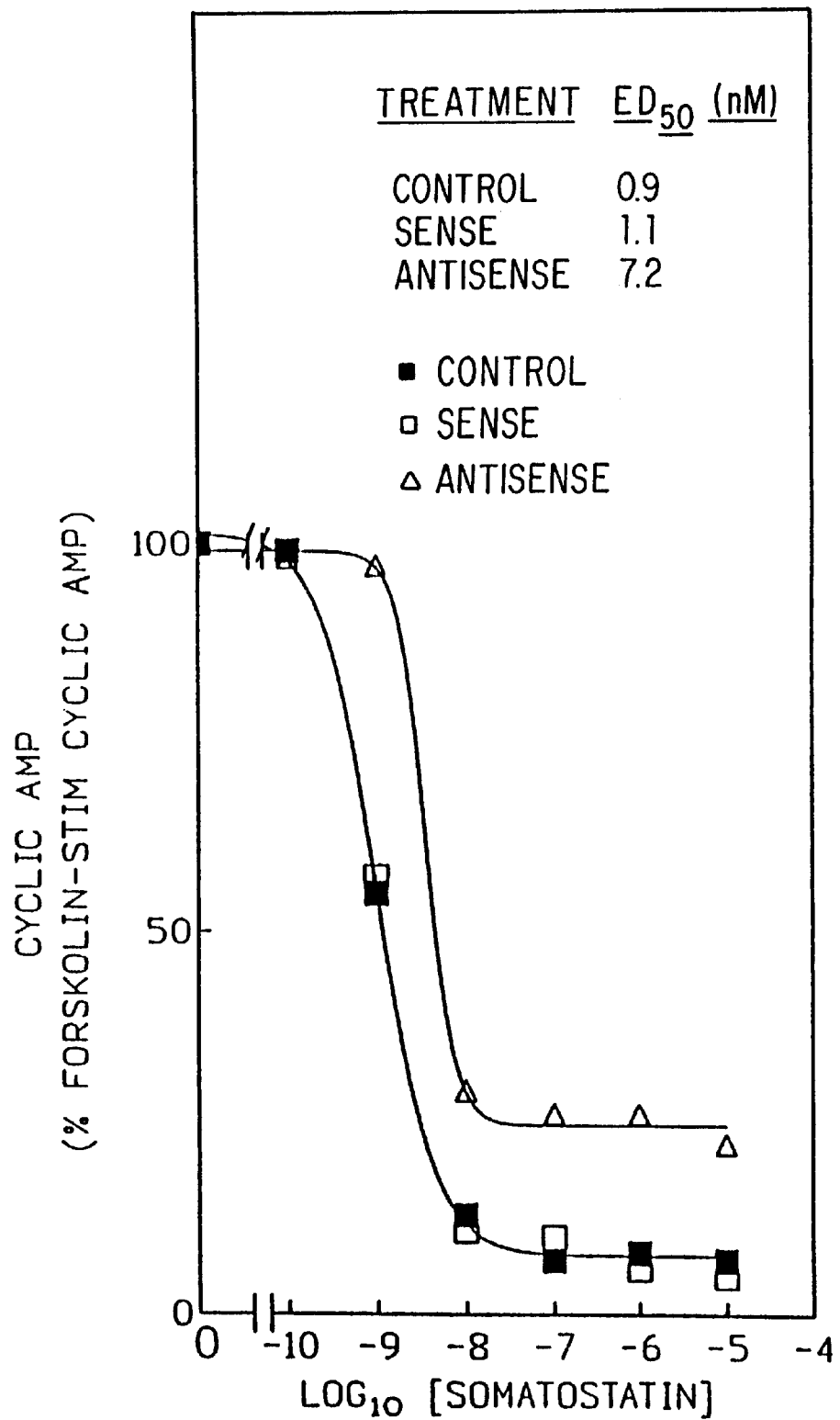

FIG. 6. Antisense oligonucleotide inhibition of somatostatin receptor function in AtT20 corticotrophs. AtT20 corcitotrophs are treated with vehicle (control), a sense oligo (5 μM), or an antisense oligo (5 μM) directed against the orphan G-protein-linked receptor PCR11 for 24 hours. The cells are harvested and somatostatin-mediated inhibition of cyclic AMP response curve performed three times with equivalent results. The lower panel is the average of three separate experiments.

FIG. 7. Nucleotide sequence of mouse SSTR3 DNA fragment. Underlined sequences indicate PCR primers. Oligo #8 anchors the 5' terminus and oligo #12 is the 3' terminus.

FIG. 8. Alignment of somatostatin receptor peptides. Amino acid sequences of SSTR1 and SSTR2 are aligned to SSTR3. Lines above the sequences indicate hydrophobic transmembrane domains. Only sequences from transmembrane region 2 to transmembrane region 7 are shown. Small case letters indicate conservative amino acid substitutions; upper case letters indicate nonconservative changes. To maximize the alignments, three residues near the C-terminus of transmembrane domain 4 of SSTR1 and SSTR2 are deleted. Additionally, SSTR1 has 1 fewer residue in tm6 and 3 fewer in tm7.

DETAILED DESCRIPTION OF THE INVENTION

The present method can be employed to isolate and clone nucleotide sequences encoding proteins from any family of proteins for which (1) a consensus sequence or sequences can be identified; (2) a cell line expressing the protein is available; and (3) a functional assay exists. However, the method is particularly useful in isolation of the nucleotide sequences encoding various types of receptors. Although the specific examples provided in this application relate to isolation and identification of a nucleic acid fragment encoding a G protein-linked receptor for a small peptide hormone, those skilled in the art will readily recognize how the techniques described herein can be applied to other receptors as well.

The first step of the method employs the polymerase chain reaction (hereinafter "PCR") to amplify the amount of receptor nucleic acid available for study. The nucleic acid used in the PCR is not restricted to any particular source, but the source cells will preferably be obtained from tissue which is known to express a particular receptor or receptors of interest. Tissue sources for various receptors are well known in the art, as seen, for example in Trends in Pharmacological Sciences, Receptor Supplement, January 1992 (24). Once an appropriate target cell or tissue type is identified, genomic DNA, cDNA, either from a library or synthesized from RNA, or RNA itself is isolated therefrom by standard methods (20), in preparation for use as a template for PCR.

The technique of PCR is described in U.S. Pat. Nos. 4,683,202; 4,683,195; and 4,965,188; the contents of these patents are incorporated herein by reference. In brief, PCR is useful in amplifying, cloning and/or detecting a target sequence in a sample of DNA. Typically, the native duplex DNA strand is denatured, so that the individual strands separate. The separate strands each constitute a template which is contacted with primers, which are usually oligonucleotides designed to be able to anneal with a portion of the target sequence contained on the template. The primers of each strand are then extended by the use of DNA polymerase, thereby providing two new copies of the target sequence. The entire process is repeated numerous times, thus potentially resulting in millions of copies of the targeted sequence, making detection of a gene expressed at very low levels considerably easier.

As applied to the present method, the template nucleic acid is derived from a cell known or expected to carry nucleic acid encoding one or more receptors of interest. The nucleic acid is then contacted with primers (oligos) specifically designed to anneal with sequences characteristic of the receptor or receptors of interest. For example, in the examples provided herein, comparison of the known nucleotide sequences (see generally 19), particularly of somatostatin (25), substance K (23), substance P (23, 6, 26, 4, 21), neuromedin K (22), thyrotropin (8, 9, 17, 19), LH/hCG (12, 14, 16), and other receptors designated mas (27), mrg and rta indicates from regions exhibiting a significant degree of conservation. From this observation, five oligonucleotide primers are designed; with 4- to 64-fold degeneracy plus 5–23% inosines. (See FIG. 2A. SEQ. ID. NOS. 9–13). These oligos are capable of recognizing virtually any receptor for a peptide ligand in the PCR procedure, and indeed, as shown below, are used to isolate the sequence encoding a novel somatostatin receptor. Other heretofore unisolated receptor genes which may be cloned using these oligos include, but are not limited to, the receptors, CRF (corticotropin release GNRH (gonadotropin release hormone), follitropin release hormone, growth hormone releasing hormone, octopamine, galanin, adenosine subtypes, angiotensin (II) subtypes monocyte chemoattractant protein-1, and vasopressin subtypes.

If a different type of receptor is sought, alternate oligos can readily be constructed. For example, to identify genes encoding the secretin type of receptor (which are structurally similar to the peptide hormone receptors, but have quite distinct amino acid sequences), a comparison of the secretin, calcitonin and parathyroid receptor gene sequences provide the information for design of four novel oligos which can be used in recognition of receptors of this subclass (FIG. 2B) SEQ. ID. NOS. 14–17. This group of receptors potentially includes secretin, calcitonin, parathyroid hormone, growth hormone releasing factor (GRF) and glucagon.

For the identification of amine receptors, a number of oligos have already been described (8). Similarly, appropriate sequences for odorant receptors have also been described (2). In each case, these can be used in the same manner as the oligos described above.

The foregoing lists relate to G protein-linked receptors, but oligos for use in this method can also be made for other types of receptors, e.g., non G protein-linked peptide hormone receptors and steroid hormone receptors. The appropriate oligonucleotides can be designed by comparison of several known related genes of that receptor type to determine regions of homology among them, then creating degenerate oligos based on one or more of these consensus sequences.

In the PCR procedure, the number of primers used is not critical and, to some extent, will be governed by the number of useful oligos available for this purpose. Generally, optimal primer number is determined empirically, dependent on the results obtained with a first pair of primers used.

Typically, a balance is struck between the number of oligo pairs, the number of homologous sequences present in each receptor subclass to which oligos may be directed, and the facilities available to analyze the products.

The conditions for PCR reactions are well known in the art. The resulting clones are then isolated and the nucleotide sequence determined for all or part of the clone. At this point, the clone still represents an "orphan", the identity of which remains to be determined. However, it can be determined at this time whether the peptide encoded by the clone has the general hallmarks of a receptor molecule, particularly of the receptor type originally selected for. For example, membrane bound receptors are arranged in a pattern of intracellular (IC), external and transmembrane (TM) domains, though the types of these domains are specific to each group of receptors. The presence of the characteristic domains can be determined from the predicted amino acid sequence by analysis by the Kyte-Doolittle hydropathy index (7; See also FIG. 4). Once the protein has been confirmed as likely being a receptor, its subclass identity can be somewhat further refined before proceeding to the next stage of the process. A relatively short (i.e., 8–23 amino acids) third intracellular loop (IC3), for example, is characteristic of G protein-linked peptide ligand receptors; in contrast, the IC3 of amine receptors generally has about 47–155 residues, and contain a conserved Asp residue in their third transmembrane domain. Although this determination is not essential to the success of the method, it will help to screen out clones which are not likely to have been derived from receptor DNA, and to select for those that are likely to be receptor-derived.

In order to more specifically determine the identity of the receptor, the sequence obtained from selected clones is then used to design antisense oligonucleotides. The specific length of the oligo is not critical, but it is preferable to use the largest oligo that can be taken up by cells to provide the greatest sequence specificity. Typically oligos comprise 15 to 21 nucleotides. Generally, at least two complementary oligonucleotides are made, one in the sense orientation and one in the antisense orientation. Preferably the antisense oligos are designed to correspond to regions of mRNA that display the least amount of predicted secondary structure. Each oligo preferably contains 50–70% cytosines plus guanines to maximize hybridization to mRNA. The antisense oligo is used to evaluate whether any receptor function can be blocked in a wild-type cell. If the orphan clone from which the antisense sequence is derived does represent all or part of a receptor gene, then the antisense oligo (but not the sense oligo), when provided to a cell normally capable of expressing that same receptor, should block expression of that receptor.

Since the desired subclass of receptor is determined at the start of the procedure, the type of cell used to evaluate the effect of the antisense oligo will be selected from among cells known to normally express receptors of the type and subclass initially sought. Whole cells or cell membranes from the selected cell type are treated with either an antisense oligo, its complementary sense oligo, or vehicle (as a control). The treated preparations are then observed to determine the presence or absence of receptor function in the presence of a ligand which normally binds to the receptor. In a typical situation, a variety of ligands are tested; the ligands selected for testing are those which are known to bind to receptors within the subclass sought.

The activity of a receptor in the presence of its ligand can be determined in a number of ways. The ligand can be detectably labelled, e.g., with a radioisotope, chemiluminescent molecule, or any other detectable label commonly used in the art. The labelled ligand is then contacted with the treated cells, or preferably cell membranes from treated cells, and the presence or absence of binding of the ligand to the cell or cell membranes determined. The observation of ligand binding in an antisense-treated cell indicates that the antisense oligo had no effect on expression of that ligand's receptor, thereby eliminating that receptor from consideration as being the one encoded by the orphan clone. on the other hand, the absence or reduction of bound ligand to cell membranes from antisense treated cells, combined with the observation of ligand binding in the sense-treated cell membranes, indicates that the original orphan clone represents all or a portion of the gene encoding the receptor for that particular ligand.

Alternately, assuming that the receptors sought are of the type whose action is mediated by a second messenger, then receptor function can be evaluated by measuring accumulation of the second messenger. For example, many peptide hormones mediate their ultimate effects by way of the action of cyclic AMP (cAMP). Thus, the binding of a particular ligand to a receptor can be evaluated by measuring the accumulation of cAMP within antisense-treated intact cells. If there is no stimulation or inhibition (depending on the receptor) of cAMP accumulation in an antisense-treated cell in the presence of a particular ligand, then it can be assumed that the receptor for that ligand was not expressed, and that the orphan sequence shares identity with the receptor for that ligand. Cyclic cAMP accumulation assays are well known in the art (3, 5). However, the practice of the invention is not limited to identification of receptors for peptide hormones where activity is mediated by cAMP. other second messenger systems are also known, e.g., ion channels are detected by patch clamp, and inositol phosphates and arachidonic acid can be assayed using commercially available kits (New England Nuclear). In the case in which second messenger accumulation is used as the central indication of receptor blockage, labelled ligand binding can be used as a further confirmation of receptor identity.

If it should be the case that the original clone represents only a fragment of the receptor, further screening is necessary to isolate the entire gene. This can be easily achieved at this stage, however, because the fragment has already been conclusively demonstrated to be receptor-derived, and therefore can be reliably utilized as a probe to screen genomic or cDNA libraries for the entire receptor sequence. Alternately, a method for rapid amplification of cDNA ends (RACE; 11) permits cloning of a complete gene sequence without library screening. Sequencing and subsequent cloning of the entire sequence can be achieved using standard techniques available in the art (20). Utilizing the foregoing method, a novel somatostatin receptor is identified.

It will be understood by those skilled in the art that the present method is applicable to a wide variety of receptors. Among the receptors of particular interest are the receptors for GRP, VIP, galanin, glucagon, β-endorphin, CCKB, GHRH, GNRH, follitropin releasing hormone, CRF, octopamine, adenosine subtypes, angiotensin II subtypes monocyte chemoattractant protein-1, and vasopressin isoforms. There are also convenient, publicly available host cell lines for use in the antisense assay: for example, Rin cells provide a source of expressed glucagon and galanin receptors; RC-4B cells are a useful cell line for GRF, GHRH, GNRH, and follitropin releasing factor receptors. NG108 cells are a source of β-endorphin receptor. AtT20 cells can be used in connection with CRF receptor. Neuroblastoma cells are a convenient source for CCKB.

In addition to those receptors and cell lines noted above, variations of the claimed method will also be apparent to those skilled in the art.

The invention is further illustrated in the following non-limiting examples.

EXAMPLES

1. General Methods

Unless otherwise specified, the following metbods are utilized in the procedures described below:

Polymerase Chain Reaction. Oligonucleotides are synthesized on an Applied Biosystems Model DNA synthesizer. PCR reactions are done with the Perkin-Elmer Cetus Gene-Amp® PCR kit if using DNA as the template or with the same manufacturer's GeneAmp® rTth RNA PCR kit if using RNA as the template. Reactions are performed, but not limited to, the manufacturer's recommendations with a 39° C. annealing temperature for degenerate oligonucleotides or 60° C. for specific primers. Each reaction contains 1 µg DNA or total cellular RNA plus 1 µg of each primer (ca. 1 µM final concentration).

Sequence Analysis. PCR products are separated in a 1.2% agarose slab gel containing 1 µg/ml ethidium bromide. DNA fragments of the expected length are cut out and purified with GeneClean® (BIO101). The termini are polished with T4 DNA polymerase in the presence of 0.25 mM dNTPs and ligated into pGEM3Z (Promega Corp.) cleaved with SmaI. Selected clones are sequenced using the Applied Biosystems dye primer DNA sequencing kit and the Applied Biosystems Model 373A automated sequencer. Protocols are as recommended by Applied Biosystems. Nucleotide sequences are analyzed with the MacVector® software package.

2. Isolation of Receptor Fragments

To target peptide receptors, consensus sequences are identified from nine rat genes. These sequences are then utilized to design probes for the isolation of new genes of the peptide receptor class. The receptors used are those for somatostatin, substance K, substance P, neuromedin K, thyrotropin, LH/CG and others designated mas, mrg, and rta. Four regions of nucleotide sequence are found to exhibit a degree of conservation significant enough to design degenerate oligonucleotide primers for PCR. Five oligos are designed with 4- to 64-fold direct degeneracy plus 5% to 23% inosines (FIG. 2A) SEQ. ID. NOS. 9–13. Additional probes are developed for the class of G protein-linked receptors characterized by the rat secretin receptor. This class currently has only four known members (recognizing secretin, calcitonin, parathyroid hormone and vasoactive intestinal peptide). The sequences for these genes are aligned and four oligonucleotides are subsequently designed to potentially recognize this subtype (FIG. 2B) SEQ.ID. NOS. 14–17. Neither set of oligos would be predicted to amplify amine receptor sequences.

Figure 2A:
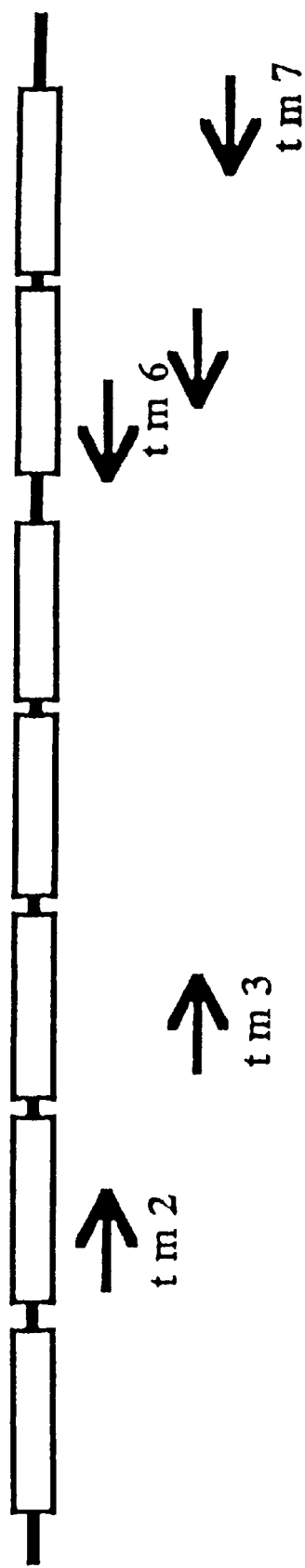
FIG. 2. Description of oligonucleotides used as PCR primers. Lines with boxes represent genes encoding G protein-linked receptors. Each box indicates a transmembrane domain. Arrows correspond to binding sites for the described oligos. Nucleotide sequences use the IUPAC-IUB nomenclature for incompletely specified bases. A. Oligonucleotides directed toward the general class of peptide ligand receptors. B. Oligonucleotides directed toward the secretin receptor-like subclass.
Figure 2B:
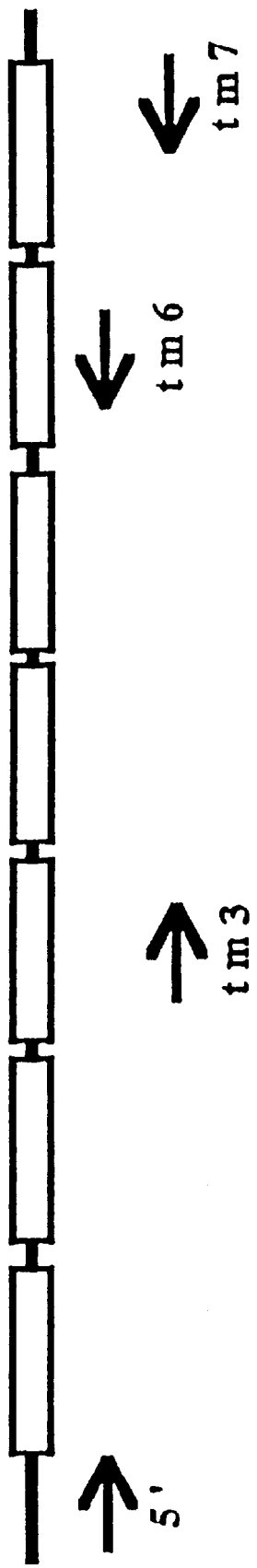
Figure 4A:
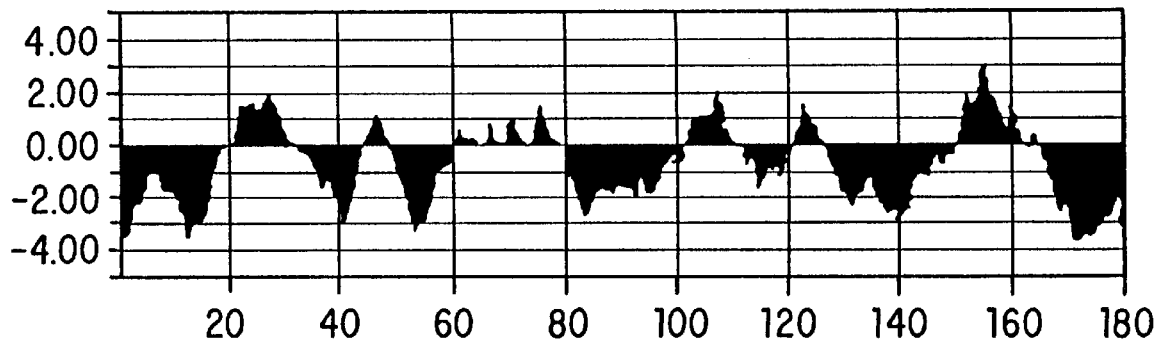
FIG. 4. Hydropathy plots of peptides encoded by novel PCR fragments. The peptide product of each PCR fragment is analyzed by the Kyte-Doolittle hydropathy index. Each sequence begins within the second transmembrane domain and ends in the sixth transmembrane domain. Hydrophobic transmembrane domains 3, 4, and 5 are readily apparent. The plot derived from the comparable region of a rat somatostatin (SRIF) receptor is shown for comparison.
Figure 4B:
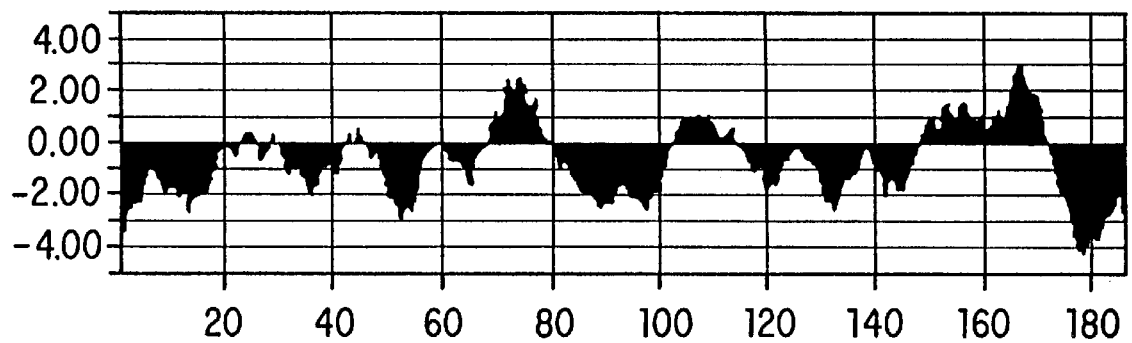
Figure 4C:
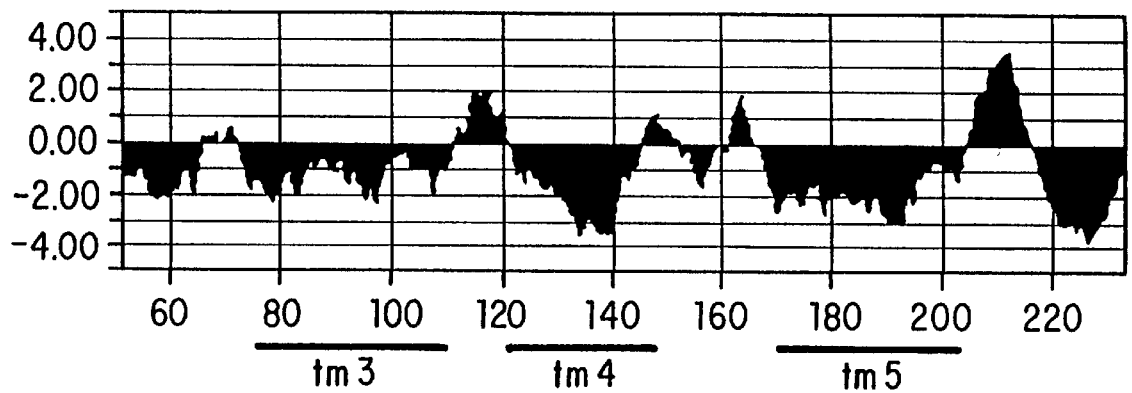

The five oligos described in FIG. 2A are designed to anneal sequences in G protein-linked peptide receptor genes. Oligos are synthesized on an Applied Biosystems Model DNA synthesizer. The oligos are used as six different primer pairs for PCR. PCR reactions are conducted as described above. Using rat genomic DNA as the template, all six reactions produce DNA fragments of the expected size (ranging from ca. 420 bp for a tm3 to tm6 fragment to ca. 700 bp for a tm2 to tm7 fragment), DNA fragments are cloned and two samples, designated PCR9 and PCR11, are found to contain sequences characteristic of G protein-linked receptors but no exact matches are found in GenBank (Table 1). Nucleotide sequences of these two fragments are shown in FIG. 3 SEQ. ID. NOS. 1–2. Each fragment contains a single open reading frame. The comparison with other receptor sequences shows a considerable similarity between a rat somatostatin receptor and PCR 11, suggesting that PCR11 is a novel somatostatin receptor subtype. Both fragments exhibit not only primary sequence similarity to other receptors but also the hydropathy pattern characteristic of G protein-linked receptors (FIG. 4). Interestingly, the predicted third intracellular loop (IC3) of each new sequence is comparatively short, a hallmark of peptide receptors which have IC3s of 8 to 23 amino acids long (PCR #9 has an IC3 of 13 residues and PCR #11 has one of 23 amino acids). In contrast, the IC3s of amine receptors range from 47 to 155 residues in length. These observations suggest that the novel G protein-linked receptors represented by the PCR products are of the peptide ligand subclass.

TABLE 1

Relatedness of Novel PCR Fragments to G Protein-Linked Receptors[a]

| Receptor Class | Gene Designation[b] | PCR #9[c] | PCR #11[c] |
| --- | --- | --- | --- |
| Peptide Ligand | srif | 37 | 57 |
|  | neuK | 24 | 30 |
|  | subK | 22 | 25 |
|  | subP | 20 | 26 |
|  | mas | 23 | 16 |
|  | mrg | 15 | 18 |
|  | thy | 19 | 18 |
|  | lhcg | 16 | 13 |
| Amine Ligand | α1b | 21 | 27 |
|  | β2 | 24 | 20 |
|  | d2 | 10 | 22 |

Notes:
[a]Each PCR fragment (designated #9 or #11) is translated and compared to G protein-linked receptors available in GenBank.
[b]All sequences are from rat. Designations are: srif, somatostatin receptor; neuK, neuromedin K receptor; subK or P, substance K or P receptor; mas, mas oncogene; mrg, mas related gene; thy, thyrotropin receptor; lhcg, luteinizing hormone and chorionic gonadotropin receptor; α1b, $α_{1b}$-adrenergic receptor; β2, $β_2$-adrenergic receptor; d2, $D_2$ dopamine receptor.
[c]Numbers represent the percent identical or conserved amino acids over the length of the translated PCR fragment. Any percentage greater than 15 is considered highly significant.

Figure 5:
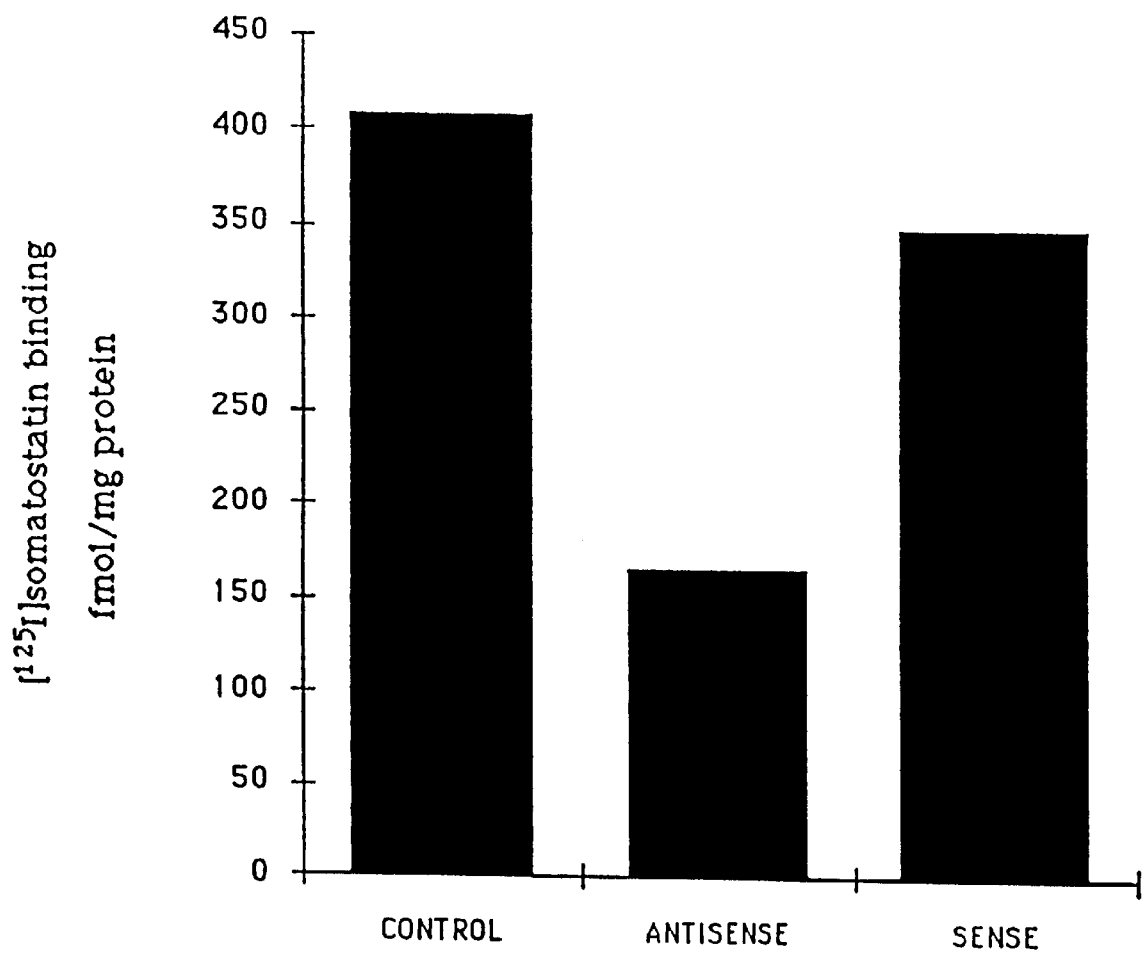
FIG. 5. Antisense oligos block expression of somatostatin receptors in $GH_4 C_1$ cells: analysis by radioligand binding. $GH_4C_1$ cells are treated with vehicle (CONTROL), an antisense DNA or the corresponding sense strand for 24 hours as described in the text. The cells are harvested, crude plasma membranes are prepared and radioligand binding is performed using [$^{125}$I]somatostatin (50 fmol/tube, 250 pMol final). Non-specific binding is determined in the presence of 1 μM somatostatin. The results displayed are the average of two separate experiments, performed in triplicate.

3. Blockade of Somatostatin Receptor and Expression Expression Function with Antisense Oligos A. Ligand Binding Assay $GH_4C_1$ (a pituitary cell line) cells are grown to 50% confluence in 10% fetal bovine serum, Dulbecco's modified Eagles medium in a humidified chamber (37° C., 95:5, air $CO_2$). The $GH_4C_1$ cells are then incubated with vehicle ($H_2O$) (control), with an antisense oligo (18 mer, GGGTCGCCTCCATTTCGG, 5 µM) (SEQ. ID. NO.:5), or the complementary sense strand (18 mer, GCCAAATGGAGGCGACCC, 5 µM) (SEQ.ID.NO.:6) for 4 hours at 37° C. (95:5, air $CO_2$) in Dulbecco's modified Eagles medium without serum. At the end of the 4-hour time period, heat-inactivated fetal bovine serum is added to 10% (final concentration). The cells are grown for an additional 20 hours. The cells are harvested, crude membranes are prepared as described by Eppler et al. (28). Radioligand binding is performed with [$^{125}$I]tyr-somatostatin, S-14 (50 fmol/tube, 250 pMol final), using standard binding assay methods as follows: binding assays are done in a binding buffer containing 50 mM HEPES (pH 7.4), 0.5% BSA and 5 mM $MgCl_2$. The standard filtration assay for [$^{125}$I]SRIF analog binding to $GH_4C_1$ membranes is carried out as follows: 1. Radioligand is diluted in binding buffer+PMSF/Baci to the desired cpm per vol. of 10 µl and then 180 µl aliquots are added to the table. For non-specific binding samples, 10 μl of 20 μM cold S14 is also added per well of membrane diluted to the desired concentration (10–30 ug membrane protein/well) in binding buffer+PMSF/Baci. Binding is stopped by rapid filtration of samples through Whatman GF/C filters presoaked with 0.3% polyethyleneimine. Binding is allowed to proceed at 30° C. for 1–2 hours. Binding is stopped by rapid filtration of samples through Whatman GF/C filters presoaked with 0.3% polyethyleneimine. Each sample is washed three times with ice-cold binding buffer (5 ml). Finally the individual wells are placed in 12×75 mm tubes and counted in an LKB Gammamaster counter (78% efficiency). The results, displayed in FIG. 5, are the average of two experiments, each performed in triplicate. It can be seen that membrane from cells treated with vehicle and the sense oligo display equivalent levels of binding ([$^{125}$I]tyr-somatostatin (408 v 350 fmol/mg). In membranes challenged with the antisense oligo for 24 hours, a 60% decline in [$^{125}$I]tyr-somatostatin binding is observed (166 mol/mg). Thus blockade of receptor expression with antisense, but not the sense oligos shows a specific means by which loss of function can be used to characterize and identify orphan receptors.

B. cAMP Assay

AtT20 cells are grown to 50% confluence in 10% fetal bovine serum, Dulbecco's modified Eagles medium in a humidified chamber (37° C., 90:10, air:$CO_2$). The AtT20 cells are then incubated with vehicle (control), with an antisense oligo directed against the orphan G protein-linked receptor PCR11 (20 mer, CGAGCGCCTCCGCCTTGAGG, 5 μM) (SEQ ID. NO.:7), or the sense strand (20 mer, ACGCAGAACGCCGTCTCCTA, 5 μM) (SEQ. ID.NO.:) for 4 hours at 37° C. (90:10, air:$CO_2$) in Dulbecco's modified Eagles medium without serum. The mRNA encoding this orphan receptor is detected in AtT-20 mouse pituitary cells by PCR Northern analysis. At the end of the four-hour time period, heat-inactivated fetal bovine serum is added to 10% (final concentration). The cells are harvested and bovine serum is added to 10% (final concentration). The cells are harvested and resuspended in Kreb's Ringer phosphate buffer containing 2 mM $CaCl_2$, 100 μM isobutyl-methylxanthine (to inhibit cyclic AMP-dependent phosphodiesterase activity). Somatostatin-mediated inhibition of forskolin-stimulated cyclic AMP accumulation is performed in intact cells. Cyclic AMP is measured using a kit purchased from Amersham. Cells are washed two times with Kreb's Ringer Phosphate (KRP) buffer containing 1 mM $CaCl_2$. The cells (50–100,000/tube in triplicate) are incubated for 15 minutes with activators and/or inhibitors of adenylyl cyclase in KRP buffer (final vol=100 μl) containing 100 μM isobutyl-methylxanthine. The reaction is terminated by addition of 10 μl of 0.1 N HCl. The samples are boiled for 5 minutes and then neutralized with 0.1 N NaOH containing 100 mM Tris, pH 7.5. To each tube [$^3$H] cyclic AMP is added (~15,000 cpm) and 10 μl of adrenal binding protein. The samples are incubated on ice for 90 minutes with standards, activated charcoal (100 μl) is added, and centrifuged (4° C., 2000×g for 5 minutes). The samples are compared against standards of known concentrations and quantified by liquid scintillation spectrometry. Results are depicted in FIG. 6. The figure shows that the efficacy of somatostatin mediated inhibition of cAMP accumulation is attenuated. Also, the ED50 for thet somatostatin medicated response is shifted to the right. It control and sense treated cells, the ED50s for somatostatin receptor are calculated to be 1 and 1.2 nM, respectively. In the cells treated with antisense oligos, the ED50 response to somatostatin is 9 nM, a 9-fold shift in potency. These data indicate that both the efficacy and potency of somatostatin are altered by treatment of cells with antisense oligos. Thus, the PCR11 fragment appears to identify a novel somatostatin receptor subtype. The fragment is compared with known somatostatin receptor subtypes SSTR1 and SSTR2 (25). Over the region currently available (representing greater than 50% of the coding sequence), the SSTR3 receptor is 57% identical to SSTR2, and is 74% homologous if conservative amino acid substitutions are considered (FIG. 8) SEQ. ID. NO. 4; SSTR3 is only slightly less homologous to SSTR1: 49% identical and 70% identical or conserved residues.

In the course of further experiments, a mouse homologue is also isolated. The nucleotide sequence of this fragment is given in FIG. 7 SEQ.ID. NO. 3.

DEPOSIT OF BIOLOGICAL MATERIALS

The following materials have been deposited on Jun. 4, 1992, under the terms of the Budapest Treaty, at the American Type Culture Collection, and given the indicated accession numbers.

| Description | Accession No. |
| --- | --- |
| E. coli K-12, OZ9 (PCR9) | 69005 |
| E. coli K-12, OZ11 (PCR11) | 69006 |

BIBLIOGRAPHY

1. Akamiza, T. et al., PNAS USA, 87:5677–5681, 1990.
2. Buck, L. and Axel, R., Cell, 65:175–187, 1991.
3. Czech, J. et al., J. Clin. Invest., 66:574–582, 1980.
4. Gerald, N. P., J. Biol. Chem., 265:20455–20462, 1990.
5. Hadcock, J. H. et al., J. Biol. Chem., 264:13956–19361, 1989.
6. Hershey, A. D., and Krause, J. E., Science, 247:950–962, 1990.
7. Kyte, J. and Doolittle, R. F., J. Mol. Biol., 157:105–132, 1982.
8. Libert et al., Science, 244:569–572, 1989.
9. Libert, F. et al., BBRC, 165:1250–1255, 1989.
10. Libert, F. et al., Mol. Cell Endocrinol., 68:1215–1217, 1990.
11. Lohman, M. A. et al., PNAS USA, 85:8998–9002, 1988.
12. Loosfelt, H. et al., Science, 245:525–528, 1989.
13. Masu, Y. et al., Nature, 329:836–838, 1987.
14. McFarland, K. C. et al., Science, 245:494–499, 1989.
15. Meyerhof, W. and Richter, D., FEBS Lett. 266:192–194, 1990.
16. Minigishi, T. et al., BBRC 172:1049–1054, 1990.
17. Misrahi, M. et al., BBRC, 166:394–403, 1990.
18. Nagayama, Y., et al., BBRC, 165:1184–1190, 1989.
19. Probst, W. C. et al., DNA and Cell Biology, 11:1–20, 1992.
20. Sambrook et al., Molecular Cloning. Cold Spring Harbor Laboratory, 1989.
21. Sasai, Y. and Nakanishi, S., BBRC, 165:695–702, 1989.
22. Shigemoto, R. et al., J. Biol. Chem., 265:623–628, 1990.
23. Sundelin, J. B. et al., Eur. J. Biochem. 203:625–631, 1992.
24. Trends in Pharmacological Sciences. Receptor Supplement, Elsevier, January 1992.
25. Yamada, Y. et al., PNAS USA, 89:251–255, 1992.
26. Yokotu, Y. et al., J. Biol. Chem., 264:17649–17652, 1989.
27. Young, D., PNAS USA, 85:5339–5342, 1988.
28. Eppler, C. M. et al., J. Biol. Chem., (in press), 1992.

What we claim is:

1. A method for isolation and identification of nucleic acid fragments encoding a receptor comprising:

(a) contacting a template nucleic acid, in a polymerase chain reaction, with at least one target receptor-specific oligonucleotide primer, and isolating a nucleic acid fragment resulting from the reaction;

(b) providing an antisense oligonucleotide based on a nucleotide sequence from the isolated fragment to a cell capable of expressing a particular receptor; and (c) observing the presence or absence of the particular receptor's expression in that cell wherein at least one primer is selected from Seq ID NOS. 9–17.

2. The method of claim 1 in which the receptor has a peptide ligand.

3. The method of claim 2 in which step (a) utilizes at least one primer selected from the group depicted in FIG. 2A Sequence I.D. NOS. 9–13 herein.

4. The method of claim 1 in which the receptor is a secretin type of receptor.

5. The method of claim 4 in which step (a) utilizes at least one primer selected from the group depicted in FIG. 2B Sequence I.D. NOS. 14–17 herein.

6. The method of claim 1 in which presence or absence of receptor expression is determined by a cyclic AMP assay.

7. The method of claim 1 in which presence or absence of receptor expression is determined by a ligand binding assay.

* * * * *